US012613189B2

(12) United States Patent
Maeda

(10) Patent No.: US 12,613,189 B2
(45) Date of Patent: Apr. 28, 2026

(54) METHOD FOR SENSING METHYL SALICYLATE, METHYL SALICYLATE SENSOR, AND METHOD FOR DETECTING PATHOGEN INFECTION OF CROPS USING TERBIUM-SULFOXIDE COMPLEX

(71) Applicant: NEC Corporation, Tokyo (JP)

(72) Inventor: Katsumi Maeda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 543 days.

(21) Appl. No.: 18/200,066

(22) Filed: May 22, 2023

(65) Prior Publication Data

US 2023/0384219 A1 Nov. 30, 2023

(30) Foreign Application Priority Data

May 25, 2022 (JP) ................................ 2022-085419

(51) Int. Cl.

| | |
|---|---|
| ***A01N 59/00*** | (2006.01) |
| ***C07C 317/04*** | (2006.01) |
| ***C07C 317/14*** | (2006.01) |
| ***C07F 5/00*** | (2006.01) |
| ***G01N 21/64*** | (2006.01) |
| ***G01N 21/78*** | (2006.01) |
| ***G01N 33/48*** | (2006.01) |
| *C07C 233/55* | (2006.01) |

(52) U.S. Cl.

CPC ........... *G01N 21/64* (2013.01); *C07C 233/55* (2013.01); *G01N 2021/6497* (2013.01)

(58) Field of Classification Search

CPC ........... G01N 21/64; G01N 2021/6497; G01N 21/78; G01N 33/48; C07C 233/55; C07C 317/04; C07C 317/14; C07F 5/00

See application file for complete search history.

(56) References Cited

FOREIGN PATENT DOCUMENTS

| | | | |
|---|---|---|---|
| CN | 1464027 | A | 12/2003 |
| WO | 2019/082942 | A1 | 5/2019 |
| WO | 2021/153513 | A1 | 8/2021 |
| WO | 2021/246480 | A1 | 12/2021 |

OTHER PUBLICATIONS

JP Office Action for JP Application No. 2022-085419, mailed on Dec. 16, 2025 with English Translation.

Wen-Xian Li et al., "Enhanced Fluorescence of Tb(III), Dy(III) perchlorate by salicylic acid in bis(benzoylmethyl) sulfoxide complexes and luminescence mechanism", Journal of Luminescence, 2010, vol. 130 No. 8, pp. 1455-1465.

Hiroki Iwanaga et al., "Novel Tb(III) Complexes with Hexyl Salicylate and Asymmetric Bis-phosphine Oxide Ligand", Proceedings of the 57th Meeting of the Japan Society of Applied Physics, 17a-ZL-3, 2010, https://www.jstage.jst.go.jp/article/jsapmeeting/2010.1/0/2010.1_2413/_article/-char/ja/.

*Primary Examiner* — Charles Capozzi
*Assistant Examiner* — Michael Stanley Gzybowski
(74) *Attorney, Agent, or Firm* — Sughrue Mion, PLLC

(57) ABSTRACT

Provided is a method for sensing methyl salicylate, which is a plant hormone released when a plant is infected with a disease. One aspect of the present embodiment relates to a method for sensing methyl salicylate, including detecting a reaction product of a terbium-sulfoxide complex represented by the predetermined formula and methyl salicylate.

9 Claims, 3 Drawing Sheets

METHOD FOR SENSING METHYL SALICYLATE, METHYL SALICYLATE SENSOR, AND METHOD FOR DETECTING PATHOGEN INFECTION OF CROPS USING TERBIUM-SULFOXIDE COMPLEX

This application is based upon and claims the benefit of priority from Japanese patent application No. 2022-085419, filed on May 25, 2022, the disclosure of which is incorporated herein in its entirety by reference.

TECHNICAL FIELD

The present invention relates to a method for sensing methyl salicylate released when a plant is infected with a disease, a methyl salicylate sensor, a method for detecting disease infection of a plant, and the like.

BACKGROUND ART

It is known that plants have their own defense mechanisms that work against infection by pathogens such as filamentous fungi, feeding damage by insect pests and others, and stress due to environmental changes. Specifically, when plants are infected by pathogens, they synthesize salicylic acid, a signal substance, at the site of infection. Then, salicylic acid moves through the plant body via the sieve tube tissue and induces defense mechanisms in uninfected tissues, resulting in the development of systemic resistance to pathogens (systemic acquired resistance). Also, when plants undergo feeding damage by insect pests, they synthesize ethylene and jasmonic acid, which, in the same manner as salicylic acid, move through the plant body and induce defense mechanisms systemically (induced systemic resistance). Furthermore, it is known that plants adapt to environmental stress by synthesizing abscisic acid in the plant body in response to changes in the growth environment, such as drought, low temperature, and salt damage.

It is also known that, when plants are infected by pathogens or undergo feeding damage by insect pests, they have a mechanism to inform not only the damaged plants themselves but also the surrounding plants. Specifically, salicylic acid, which is synthesized when infected by pathogens, is methylated to be methyl salicylate, which is released from the plants as a volatile signal substance to inform the surrounding plants of the pathogen infection, thus promoting defense mechanisms in advance. Jasmonic acid, which is synthesized at the time of damage by insect pests, is also known to be methylated to be methyl jasmonate, which is a volatile signal released from the plants, inducing resistance in the surrounding plants in advance.

As described above, it is known that plants release plant hormones as signal substances when they are damaged by diseases and insect pests, and sensing such signal substances as quickly as possible makes possible early detection of damage by diseases and insect pests.

A method for early discovery of damage by sensing jasmonic acid released as a volatile signal at the time of insect pest damage, had been known. Patent Document 1 discloses a method in which a monitor plant with a luminescent protein gene is cultivated alongside a cultivated crop, and a phenomenon is utilized in which the monitor plant senses methyl jasmonate released and emits light when the crop undergoes damage by insect pests.

CITATION LIST

Patent Document

Patent Document 1: International Publication No. WO2019/082942

SUMMARY OF INVENTION

Technical Problem

An object of one aspect of the present embodiment is to provide a method for sensing methyl salicylate, which is a plant hormone released when a plant is infected with a pathogen. Another object of one aspect of the present embodiment is to provide a methyl salicylate sensor.

Solution to Problem

One aspect of the present embodiment relates to a method for sensing methyl salicylate, comprising detecting a reaction product of a terbium-sulfoxide complex represented by the following formula (1) and methyl salicylate.

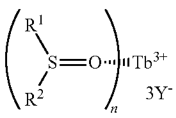

(1)

wherein $R^1$ and $R^2$ each independently represent an aliphatic hydrocarbon group having 1 to 8 carbons, or a substituted or unsubstituted aryl group. $R^1$ and $R^2$ may be bonded together to form a ring. $Y^-$ represents a carboxylate ion having 1 to 8 carbons, chloride ion, or nitrate ion. n represents an integer of 1 to 6.

Advantageous Effect of Invention

According to one aspect of the present embodiment, methyl salicylate, which is a plant hormone released when a plant is infected with a pathogen, can be selectively sensed.

DESCRIPTION OF EMBODIMENTS

Figure 1:
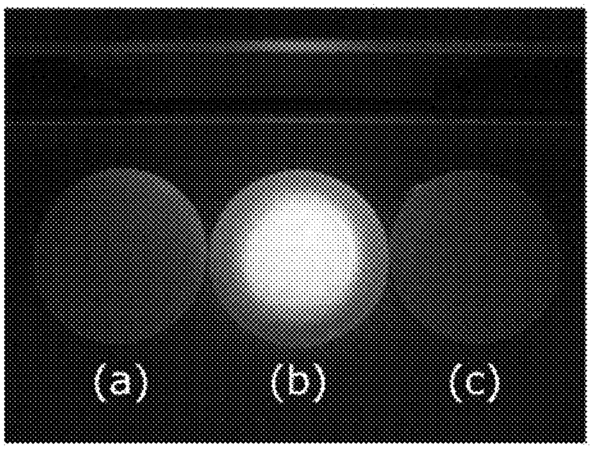
FIG. 1 shows a photograph for confirming fluorescence emission in Example 1.

Hereinafter, embodiments of the present invention will be described with reference to the accompanying drawings and others. However, while the embodiments mentioned below have technically preferred limitations for implementing the present invention, they are not intended to limit the scope of the invention to those described below.

The present inventors have conducted diligent studies in order to solve the above-mentioned problem. As a result, they have found that methyl salicylate, which is a volatile signal substance released when a plant is infected by a pathogen, can be selectively sensed by using a terbium-sulfoxide complex represented by formula (1), thus completing the present invention. Hereinafter, the present embodiments will be described in detail.

In one aspect of the present embodiment relates to a method for sensing methyl salicylate, using a terbium-sulfoxide complex represented by the following formula (1) (also simply referred to as "terbium-sulfoxide complex" or "complex represented by formula (1)") as a receptor to recognize methyl salicylate. According to the sensing method of the present embodiment, infection in a plant by a pathogen can be in-situ detected at an early stage by utilizing a fluorescence emission phenomenon from a complex formed by a reaction of methyl salicylate and the terbium-sulfoxide complex. In this specification, the complex formed by reacting the terbium-sulfoxide complex represented by formula (1) with methyl salicylate is also referred to as "methyl salicylate complex" or "MSA complex".

(1)

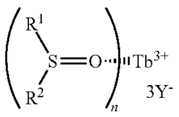

wherein $R^1$ and $R^2$ each independently represent an aliphatic hydrocarbon group having 1 to 8 carbons, or a substituted or unsubstituted aryl group. $R^1$ and $R^2$ may be bonded together to form a ring. $Y^-$ represents a carboxylate ion having 1 to 8 carbons, chloride ion, or nitrate ion. n represents an integer of 1 to 6.

<Receptor for Methyl Salicylate: Terbium-Sulfoxide Complex>

In the present embodiment, examples of the terbium-sulfoxide complex that can be used as a receptor for recognizing methyl salicylate may include a complex represented by the following formula (1). As shown in Examples below, the terbium-sulfoxide complex represented by formula (1) does not react with other plant hormones other than methyl salicylate, such as methyl jasmonate, and thus selectively recognizes methyl salicylate.

(1)

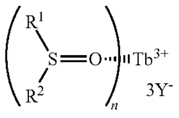

wherein $R^1$ and $R^2$ each independently represent an aliphatic hydrocarbon group having 1 to 8 carbons, or a substituted or unsubstituted aryl group. $R^1$ and $R^2$ may be bonded together to form a ring. $Y^-$ represents a carboxylate ion having 1 to 8 carbons, chloride ion, or nitrate ion. n represents an integer of 1 to 6.

In formula (1), $R^1$ and $R^2$ each independently represent an aliphatic hydrocarbon group having 1 to 8 carbon atoms, or a substituted or unsubstituted aryl group. The aliphatic hydrocarbon group having 1 to 8 carbon atoms is preferably an alkyl group having 1 to 8 carbon atoms, an alkenyl group having 2 to 8 carbon atoms, or a cycloalkyl group having 3 to 8 carbon atoms, but is not limited to these. The alkyl group having 1 to 8 carbon atoms may be linear or branched, and examples thereof include methyl group, ethyl group, propyl group, isopropyl group, n-butyl group, tert-butyl group, pentyl group, hexyl group, heptyl group, octyl group (n-octyl group, etc.) and the like, and in one embodiment, n-butyl group, tert-butyl group, or n-octyl group is preferable. Examples of the alkenyl group having 2 to 8 carbon atoms may include vinyl group, 2-propenyl group (allyl group), 3-butenyl group, 1-methylvinyl group, 2-methylvinyl group, 1-methylpropenyl group, 2-methylpropenyl group and the like, and in one embodiment, vinyl group is preferable. Examples of the cycloalkyl group having 3 to 8 carbon atoms may include cyclopropyl group, cyclobutyl group, cyclopentyl group, cyclohexyl group and the like. Examples of the substituted or unsubstituted aryl group may include phenyl group, methoxyphenyl group, dimethylaminophenyl group, thienyl group, furanyl group (furyl group), pyridyl group, and the like, and in one embodiment, phenyl group is preferable. $R^1$ and $R^2$ may be the same as or different from each other, and in one aspect, they are preferably the same. $R^1$ and $R^2$ may be attached to each other to form a ring.

In formula (1), n represents an integer of 1 to 6, preferably an integer of 1 to 3, and in one embodiment, n=2 is preferable.

In formula (1), when n is 2 or more, a plurality of $R^1$ and $R^2$ may be the same as or different from each other. When n is 2 or more, $R^1$ and $R^2$ attached to the same S atom may be bonded to each other to form a ring, or a plurality of $R^1$ and $R^2$ (preferably two groups) attached to different S atoms may be attached to each other to form a ring.

In formula (1), $Y^-$ is a monovalent anion and represents a carboxylate ion having 1 to 8 carbon atoms, chloride ion, or nitrate ion. The carboxylate ion having 1 to 8 carbon atoms is obtained by releasing hydrogen ion from a carboxy group of a carboxylic acid, and may be linear or branched. Examples of the carboxylate ion having 1 to 8 carbon atoms include a monovalent carboxylate ion such as formate ion, acetate ion, propionate ion, butyrate ion, pivalate ion and valerate ion. In one aspect, $Y^-$ is preferably acetate ion, propionate ion, butyrate ion, pivalate ion, valerate ion, chloride ion or nitrate ion, and more preferably acetate ion, pivalate ion or valerate ion.

Specific examples of the terbium-sulfoxide complex include, but are not limited to, the complexes shown in the following Table 1.

TABLE 1

| | Structural formula |
|---|---|
| Tb-S1 | 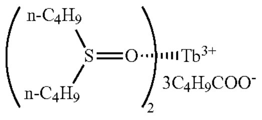 |
| Tb-S2 | 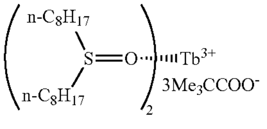 |

TABLE 1-continued

| | Structural formula |
| --- | --- |
| Tb-S3 | 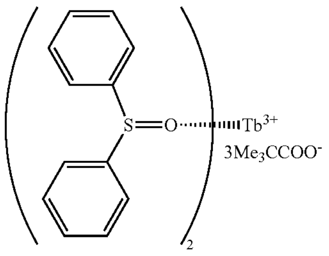 |
| Tb-S4 | 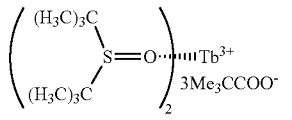 |
| Tb-S5 | 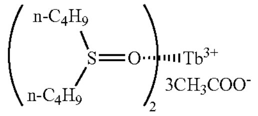 |
| Tb-S6 | 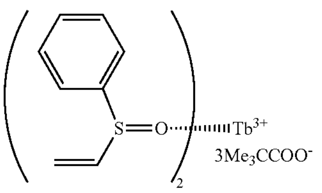 |

These terbium-sulfoxide complexes are synthesized by heating and reacting a terbium salt and a sulfoxide derivative in an organic solvent such as methanol or ethanol (see, Reaction formula (11)). The terbium salt ($TBY_3$) may be synthesized by reacting terbium chloride hexahydrate and a sodium carboxylate in water.

Reaction formula (11)

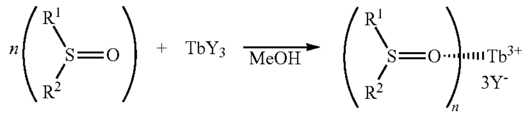

$R^1$, $R^2$, n and Y in reaction formula (11) have the same meanings as $R^1$, $R^2$, n and Y defined in formula (1), respectively.

For example, as a method for synthesizing Tb-S1, terbium valerate and di-n-butyl sulfoxide are heated to reflux in methanol as represented by the following Reaction formula (11-1) for 6 hours to form a complex of terbium valerate and di-n-butyl sulfoxide.

Reaction formula (11-1)

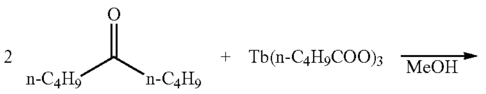

-continued

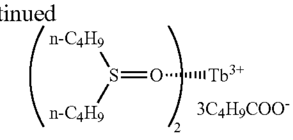

These terbium-sulfoxide complexes can selectively recognize methyl salicylate by reacting with methyl salicylate to form a methyl salicylate complex. For example, Tb-S3 forms a methyl salicylate complex by the reaction represented by the following Reaction formula (12). The resulting methyl salicylate complex exhibits fluorescence emission characteristic of the terbium complex when excited with a UV light. On the other hand, when the terbium-sulfoxide complex represented by formula (1) alone is irradiated with a UV light, fluorescence emission is not observed. Furthermore, the terbium-sulfoxide complex represented by formula (1) does not react with other plant hormones such as methyl jasmonate. By utilizing the phenomenon, the sensing method of the present embodiment can selectively recognize methyl salicylate.

Reaction formula (12)

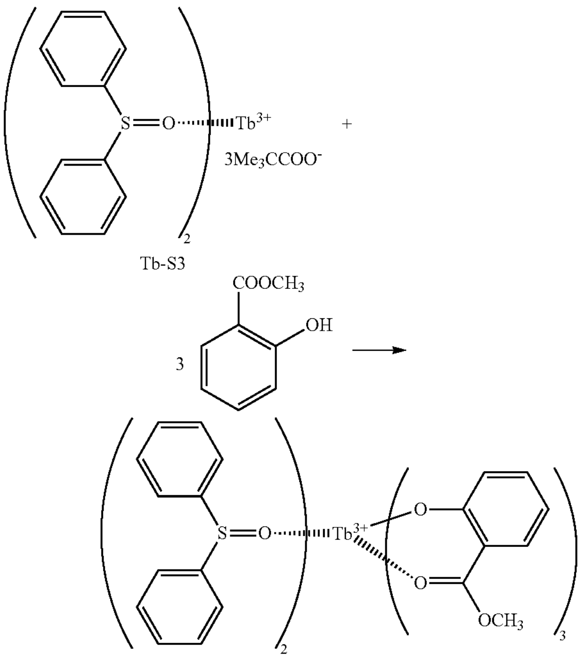

Tb-S3

One aspect of the present embodiment relates to a method for detecting methyl salicylate, comprising reacting a terbium-sulfoxide complex represented by formula (1) with methyl salicylate to form a methyl salicylate complex.

One aspect of the present embodiment relates to a method for sensing methyl salicylate using a terbium-sulfoxide complex represented by formula (1) as a receptor that selectively recognizes methyl salicylate.

In one aspect of the present embodiment, the reaction of the terbium-sulfoxide complex represented by formula (1) and methyl salicylate is carried out in a solution. The solution may be, but is not limited to, a dimethyl sulfoxide solution, an alcoholic solution such as methanol or ethanol, or an aqueous solution. In some embodiments, the concentration of the terbium-sulfoxide complex represented by formula (1) may be, for example, preferably in the range of 0.00001 mol/L to 5 mol/L, more preferably in the range of 0.00004 mol/L to 1 mol/L.

In some embodiments, the reaction of the terbium-sulfoxide complex represented by formula (1) and methyl salicylate is carried out in a solid medium comprising the terbium-sulfoxide complex. The solid medium may be, but is not limited to, paper or glass (for example, a glass fiber, a porous glass substrate), or resin (for example, polymethyl methacrylate, polyethylene, polypropylene, polyvinyl chloride, polystyrene, nylon resin, polyamide, polycarbonate, polyethylene terephthalate, polybutylene terephthalate, polyphenylene oxide) or water-soluble polymer (such as cellulose-based polymer, agarose, starch-based polymer, sodium arginate, polyacrylate-based polymer, polyacrylamide-based polymer, polyvinyl alcohol, polyethylene oxide, polyvinylpyrrolidone).

<Fluorescence Emission Phenomenon>

The complex produced by the reaction of the terbium-sulfoxide complex represented by formula (1) and methyl salicylate newly exhibits fluorescence emission. Specifically, the complex formed by the reaction of the terbium-sulfoxide complex and methyl salicylate exhibits fluorescence emission by exposing it to an excitation light with a wavelength of preferably 300 to 400 nm. On the other hand, the terbium-sulfoxide complex alone exhibits little fluorescence emission, which makes it possible to detect methyl salicylate.

Thus, some embodiments of the present invention relate to a method for detecting methyl salicylate, comprising: (i) a step of allowing a terbium-sulfoxide complex represented by formula (1) to react with methyl salicylate to form a methyl salicylate complex; (ii) a step of exposing the methyl salicylate complex to excitation light; and (iii) a step of detecting fluorescence emitted by the methyl salicylate complex. In some embodiments, an appropriate wavelength in the range of 300 to 400 nm is selected as an excitation wavelength. Furthermore, in some embodiments, a step of comparing the intensity of the detected fluorescence with a predetermined reference value to determine the concentration of methyl salicylate may also be performed.

Some embodiments of the present invention relate to a method for sensing methyl salicylate, utilizing a fluorescence emission phenomenon of a methyl salicylate complex formed by a reaction of methyl salicylate and a terbium-sulfoxide complex represented by formula (1).

In some embodiments, the method for sensing methyl salicylate of the present invention may be used for detecting pathogen infection in a crop.

<Methyl Salicylate Sensor>

Figure 6:
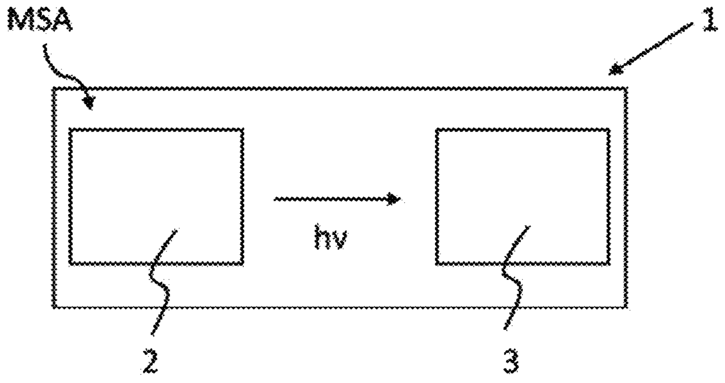
FIG. 6 is one example of a schematic diagram of the configuration of the methyl salicylate sensor of the present embodiment.

FIG. 6 shows an example of a schematic diagram of the configuration of a methyl salicylate sensor of the present embodiment. A methyl salicylate sensor 1 using the terbium-sulfoxide complex as a receptor at least comprises a receptor section 2 for methyl salicylate and a detection section 3 that detects a reaction product of the terbium-sulfoxide complex and methyl salicylate (a recognition of methyl salicylate by the receptor section 2). The receptor section 2 at least comprises the terbium-sulfoxide complex, which is a receptor. The terbium-sulfoxide complex does not react with or recognize other plant hormones other than methyl salicylate, such as methyl jasmonate, and can therefore selectively recognize methyl salicylate. The detection section 3 is configured to be able to optically detect recognition of methyl salicylate by the receptor section for methyl salicylate. For example, the optical detection section comprises at least an excitation light source (light emitting section) and a detection element (light receiving section for receiving fluorescence) in order to detect fluorescence emission of a complex (methyl salicylate complex) produced by the terbium-sulfoxide complex and methyl salicylate, and detects methyl salicylate and measures the concentration thereof based on a change in fluorescence intensity.

Thus, some embodiments of the present invention relate to a methyl salicylate sensor for detecting methyl salicylate, at least comprising: a receptor section for methyl salicylate that comprises the terbium-sulfoxide complex represented by formula (1); and a detection section that detects a reaction product of the terbium-sulfoxide complex and methyl salicylate (a recognition of methyl salicylate by the receptor section). In some embodiments, the methyl salicylate sensor of the present embodiment detects methyl salicylate, which is a plant hormone released when a crop is infected by a pathogen. Thus, the methyl salicylate sensor of the present embodiment may be used as a sensor for detecting pathogen infection in a crop.

In one aspect, the methyl salicylate sensor of the present embodiment can selectively detect methyl salicylate as compared other plant hormones such as methyl jasmonate and 3-hexenol by using the terbium-sulfoxide complex.

Some embodiments of the present invention relate to a methyl salicylate sensor for detecting methyl salicylate, at least comprising: (i) a receptor section for methyl salicylate that comprises a terbium-sulfoxide complex represented by formula (1); and (ii) a detection section that optically detects a reaction product of the terbium-sulfoxide complex and methyl salicylate (a recognition of methyl salicylate by the receptor section). In some embodiments, the optical detection section at least comprises an excitation light source and a detection element. In one aspect, the methyl salicylate sensor of the present embodiment can detect methyl salicylate and/or measure the concentration thereof based on a change in the observed fluorescence intensity.

In some embodiments, the detection section may comprise a computer that executes a program to process detection of methyl salicylate and/or measurement of the concentration thereof. Such a program may be, for example, a program that causes the computer to execute a step of receiving a signal from an optical detection element, a step of analyzing the received signal to determine the presence or absence of methyl salicylate and/or the concentration thereof, and a step of outputting the analysis result. In some embodiments, the analysis of the received signal may include comparing the received signal with a predetermined reference value to determine the presence or absence of methyl salicylate and/or the concentration thereof, for example. In some embodiments, the analysis result may be output to, for example, a display device connected to the sensor, or other equipment or the like connected via a network.

Thus, some embodiments of the present invention relate to a methyl salicylate sensor for detecting methyl salicylate, the methyl salicylate sensor at least comprising: a receptor section for methyl salicylate that comprises the terbium-sulfoxide complex represented by formula (1); and a detection section that detects a reaction product of the terbium-sulfoxide complex and methyl salicylate (a recognition of methyl salicylate by the receptor section), the detection section comprising a detection element and a computer, wherein the methyl salicylate sensor has a program that causes the computer to execute: (i) a step of receiving a signal from an optical detection element; (ii) a step of analyzing the received signal to determine the presence or absence of methyl salicylate and/or the concentration thereof; and (iii) a step of outputting the analysis result.

<Method for Detection of Pathogen Infection in Crop>

As one application of the methyl salicylate sensor of the present invention, by installing the methyl salicylate sensor near where a crop is planted and detecting methyl salicylate by the sensor, it is possible to detect pathogen infection in the crop at an early stage.

Thus, some embodiments of the present invention relate to a method for detecting pathogen infection in a crop, comprising installing the methyl salicylate sensor in the vicinity of the crop, and detecting methyl salicylate by the sensor. In some embodiments, the methyl salicylate sensor comprises: a receptor section for methyl salicylate that comprises the terbium-sulfoxide complex, which is a receptor that selectively recognizes methyl salicylate; and a detection section that detects a reaction product of the terbium-sulfoxide complex and methyl salicylate (a recognition of methyl salicylate by the receptor section). In some embodiments, the methyl salicylate sensor comprises: (i) a receptor section for methyl salicylate that comprises a terbium-sulfoxide complex represented by formula (1); and (ii) a detection section that optically detects a reaction product of the terbium-sulfoxide complex and methyl salicylate (a recognition of methyl salicylate by the receptor section).

Examples of the crop that may be the monitoring target include, but are not limited to, cucumber, watermelon, tomato, eggplant, green pepper, paprika, shishito pepper, melon, Chinese cabbage, cabbage, radish, lettuce, leek, broccoli, onion, garlic, Japanese yam, asparagus, carrot, potato, celery, tobacco, rice, and strawberry.

Examples of the disease that may be detected include, but are not limited to, ring spot disease, leaf spot, *Corynespora* target spot, leaf mold, *fusarium* wilt, root rot wilt, *Verticillium* wilt, brown root rot, gray *phytophthora* rot, root rot, black dot root rot, southern blight, damping off, brown leaf spot, downy mildew, powdery mildew, gray mold, anthracnose, scab, *Sclerotinia* rot, gummy stem blight, leaf spot, blight, mosaic disease, spotted wilt, yellow leaf curl, bacterial wilt, bacterial soft rot, bacterial canker, pith necrosis, bacterial black spot, and bacterial leaf spot, and examples of the pathogen infection that may be detected include, but are not limited to, infections caused by the causative microorganisms of the above diseases.

In the context of the present disclosure, when referring to installing the sensor in the vicinity of the crop, examples of the term "vicinity" include, but are not limited to, a distance within 2 m, within 1 m, within 75 cm, within 50 cm, within 40 cm, within 30 cm, within 20 cm, within 10 cm, or within 5 cm of the crop to be monitored, and an appropriate distance is selected as appropriate in consideration of a variety of factors. A person skilled in the art would be able to set the position of the sensor to be installed as appropriate in consideration of a variety of conditions.

Some embodiments of the present invention relate to the use of a methyl salicylate sensor in detection of pathogen infection in a crop. Some embodiments of the present invention relate to use of the terbium-sulfoxide complex in production of a methyl salicylate sensor.

EXAMPLES

Hereinafter, an embodiment of the present invention will be explained in details by using examples, but the present invention is not limited to these examples.

Synthesis Example 1

Complex of terbium valerate and di-n-butyl sulfoxide (Tb-S1)

1 g of terbium chloride hexahydrate was dissolved in 10 ml of water, a solution of 0.997 g of sodium valerate in water was added thereto, and the mixture was stirred at room temperature. The precipitated terbium valerate was separated through filtration and dried under reduced pressure to obtain 0.88 g of the desired product. Next, 0.3 g of terbium valerate and 0.211 g of di-n-butyl sulfoxide were dissolved in 30 ml of methanol and heated to reflux for 6 hours. After allowing to cool, the resultant was concentrated by an evaporator, diethyl ether was added to the residue, the mixture was filtered, and the filtrate was concentrated to obtain 0.50 g of the desired Tb-S1 which is a complex of terbium valerate and di-n-butyl sulfoxide. The reaction formula is as follows.

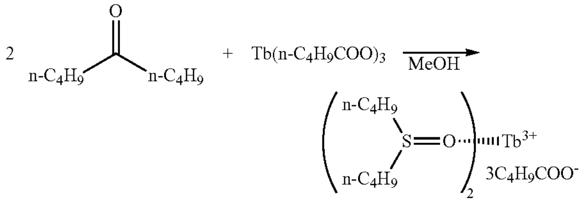

Synthesis Example 2

Complex of terbium pivalate and di-n-octyl sulfoxide (Tb-S2)

2 g of terbium chloride hexahydrate was dissolved in 20 ml of water, a solution of 2.284 g of sodium pivalate dissolved in water was added thereto, and the mixture was stirred at room temperature. The precipitated terbium pivalate was separated through filtration and dried under reduced pressure to obtain 2.094 g of the desired product. Next, 0.3 g of terbium pivalate and 0.356 g of di-n-octyl sulfoxide were dissolved in 30 ml of methanol and heated to reflux for 6 hours. After allowing to cool, the resultant was concentrated by an evaporator, diethyl ether was added to the residue, the mixture was filtered, and the filtrate was concentrated to obtain 0.64 g of the desired Tb-S2 which is a complex of terbium pivalate and di-n-octyl sulfoxide (see, Table 1 for the structural formula).

Synthesis Example 3

Complex of terbium pivalate and diphenyl sulfoxide (Tb-S3)

0.3 g of terbium pivalate and 0.263 g of diphenyl sulfoxide were dissolved in 30 ml of methanol and heated to reflux for 6 hours. After allowing to cool, the resultant was concentrated by an evaporator, diethyl ether was added to the residue, the mixture was filtered, the filtrate was concentrated to obtain 0.54 g of the desired Tb-S3 which is a complex of terbium pivalate and diphenyl sulfoxide (see, Table 1 for the structural formula).

Example 1

0.2 ml of the methanol solution (concentration: 50 mM) of the terbium valerate-di-n-butyl sulfoxide complex (Tb- S1) obtained in Synthesis example 1 was dropped onto a circular filter paper (40 mm 1) and dried to obtain three pieces of filter paper containing Tb-S1. 0.03 ml of an acetonitrile solution (concentration: 10 mM) of methyl salicylate (MSA), which is released when a plant is infected by a pathogen, was dropped onto one of the obtained filter papers and dried (b). Onto another filter paper, 0.03 ml of an acetonitrile solution (concentration: 10 mM) of methyl jasmonate (MJA), which is a signal substance released when a plant is damaged by an insect pest, was dropped and dried (c). The filter paper (a) containing only Tb-S1 (nothing dropped), the filter paper (b) in which MSA was dropped on the filter paper containing Tb-S1, and the filter paper (c) in which MJA was dropped on the filter paper containing Tb-S1 were respectively excited with a UV lamp (wavelength 365 nm) to confirm whether fluorescence emission was present (FIG. 1). As a result, it was found that although Tb-S1 alone does not exhibit fluorescence emission (a), Tb-S1 reacts with methyl salicylate to exhibit fluorescence emission and can sense methyl salicylate (b). In addition, it was found that Tb-S1 does not react with methyl jasmonate and does not exhibit fluorescence emission (c). From the above results, it was found that Tb-S1 can selectively sense methyl salicylate, which is released when a plant is infected by a pathogen.

Example 2

Figure 2:
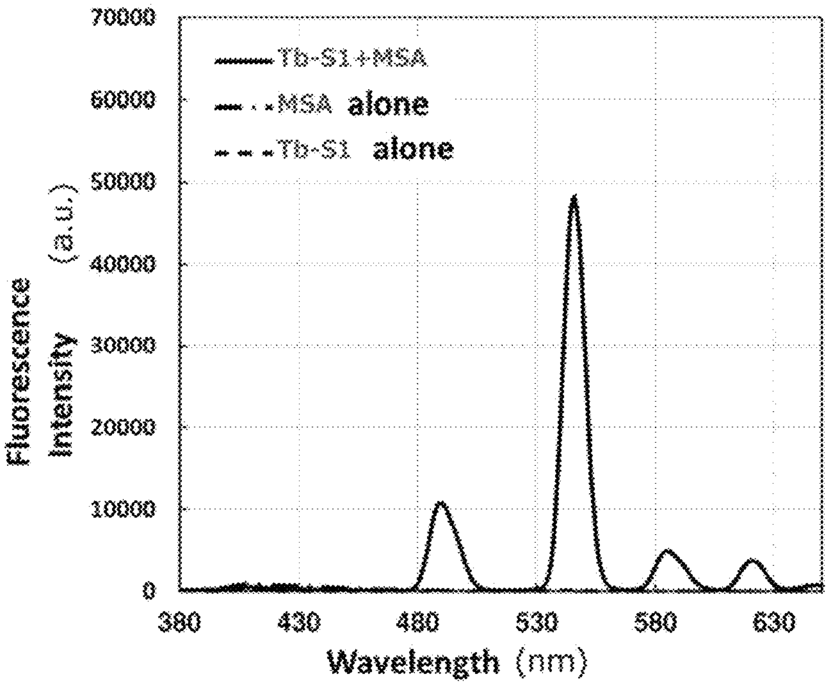
FIG. 2 shows fluorescence spectrum curves obtained by measuring in Example 2.

Fluorescence Spectrometry 0.9 ml of a dimethyl sulfoxide (DMSO) solution of a complex of terbium valerate and di-n-butyl sulfoxide (Tb-S1) (concentration: 1.7 mM) and 0.1 ml of a DMSO solution of methyl salicylate (MSA) (concentration: 1.5 mM) were mixed, and after 10 minutes, the mixed solution was diluted by 20 times. Thereafter, the resulting solution was put in a quartz cell and the fluorescence spectrum was measured at an excitation wavelength of 365 nm. Also, 0.9 ml of DMSO solution of Tb-S1 (concentration: 1.7 mM) and 0.1 ml of DMSO were mixed, the mixed solution was further diluted by 20 times, the resulting solution was put in a quartz cell, and the fluorescence spectrum was measured at an excitation wavelength of 365 nm. Similarly, 0.1 ml of DMSO solution of MSA (concentration: 1.5 mM) was mixed with 0.9 ml of DMSO, the mixed solution was further diluted by 20 times, and the resulting solution was put in a quartz cell, and the fluorescence spectrum was measured at an excitation wavelength of 365 nm. FIG. 2 shows the fluorescence spectrum curves obtained. The solid line represents the fluorescence spectrum of Tb-S1+MSA, the dashed line represents the fluorescence spectrum of Tb-S1 alone, and the dash-dot-dash line represents the fluorescence spectrum of MSA alone. These results revealed that Tb-S1 itself does not exhibit fluorescence, but a reaction product of Tb-S1 and MSA exhibits fluorescence emission in the range of 480 to 630 nm (maximum wavelength of 546 nm). Further, it was found that MSA alone does not exhibit fluorescence emission in the range of 480 to 630 nm, but Tb-S1 reacts with methyl salicylate and exhibits fluorescence emission.

Example 3

Figure 3:
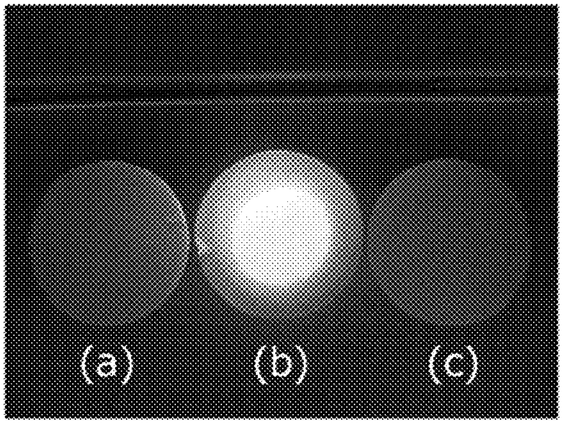
FIG. 3 shows a photograph for confirming fluorescence emission in Example 3.

0.2 ml of the methanol solution (concentration: 50 mM) of the terbium pivalate-di-n-butyl sulfoxide complex (Tb-S2) obtained in Synthesis example 2 was dropped onto a circular filter paper (40 mm 1) and dried to obtain three pieces of filter paper containing Tb-S2. 0.03 ml of an acetonitrile solution (concentration: 10 mM) of methyl salicylate (MSA), which is released when a plant is infected by a pathogen, was dropped onto one of the obtained filter papers and dried (b). Onto another filter paper, ml of an acetonitrile solution (concentration: 10 mM) of methyl jasmonate (MJA), which is a signal substance released when a plant is damaged by an insect pest, was dropped and dried (c). The filter paper (a) containing only Tb-S2 (nothing dropped), the filter paper (b) in which MSA was dropped on the filter paper containing Tb-S2, and the filter paper (c) in which MJA was dropped on the filter paper containing Tb-S2 were respectively excited with a UV lamp (wavelength 365 nm) to confirm whether fluorescence emission was present (FIG. 3). As a result, it was found that although Tb-S2 alone does not exhibit fluorescence emission (a), Tb-S2 reacts with methyl salicylate to exhibit fluorescence emission and can sense methyl salicylate (b). In addition, it was found that Tb-S2 does not react with methyl jasmonate and does not exhibit fluorescence emission (c). From the above results, it was found that Tb-S2 can selectively sense methyl salicylate, which is released when a plant is infected by a pathogen.

Example 4

Figure 4:
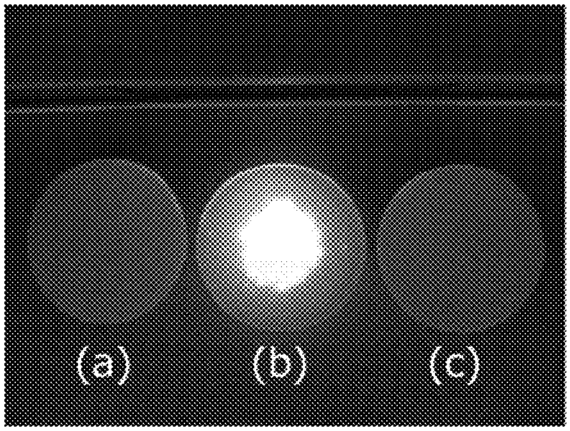
FIG. 4 shows a photograph for confirming fluorescence emission in Example 4.

0.2 ml of the DMSO solution (concentration: 50 mM) of the terbium pivalate-diphenyl sulfoxide complex (Tb-S3) obtained in Synthesis example 3 was dropped onto a circular filter paper (40 mm 1) and dried to obtain three pieces of filter paper containing Tb-S3. 0.03 ml of an acetonitrile solution (concentration: 10 mM) of methyl salicylate (MSA), which is released when a plant is infected by a pathogen, was dropped onto one of the obtained filter papers and dried (b). Onto another filter paper, ml of an acetonitrile solution (concentration: 10 mM) of methyl jasmonate (MJA), which is a signal substance released when a plant is damaged by an insect pest, was dropped and dried (c). The filter paper (a) containing only Tb-S3 (nothing dropped), the filter paper (b) in which MSA was dropped on the filter paper containing Tb-S3, and the filter paper (c) in which MJA was dropped on the filter paper containing Tb-S3 were respectively excited with a UV lamp (wavelength 365 nm) to confirm whether fluorescence emission was present (FIG. 4). As a result, it was found that although Tb-S3 alone does not exhibit fluorescence emission (a), Tb-S3 reacts with methyl salicylate to exhibit fluorescence emission and can sense methyl salicylate (b). In addition, it was found that Tb-S3 does not react with methyl jasmonate and does not exhibit fluorescence emission (c). From the above results, it was found that Tb-S3 can selectively sense methyl salicylate, which is released when a plant is infected by a pathogen.

Example 5

Figure 5:
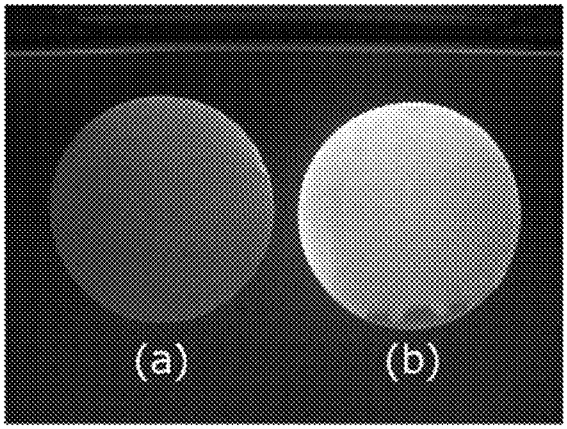
FIG. 5 shows a photograph for confirming fluorescence emission in Example 5.

0.2 ml of the methanol solution (concentration: 50 mM) of the terbium pivalate-di-n-octyl sulfoxide complex (Tb-S2) obtained in Synthesis example 2 was dropped onto a circular filter paper (40 mm 1) and dried to obtain a filter paper containing Tb-S2. The obtained filter paper was placed in a desiccator, and a gas of methyl salicylate with a concentration of 400 ppb was introduced into the desiccator with a nitrogen carrier gas. After 1 hour, the filter paper was taken out and excited with a UV lamp (wavelength 365 nm) to confirm whether fluorescence emission was present. The results are shown in FIG. 5. No fluorescence emission was observed in the filter paper (a) unexposed to methyl salicylate, but yellow-green fluorescence characteristic of the terbium complex was confirmed in the filter paper (b) after exposure for 1 hour. From the above results, it was found that Tb-S2 can detect methyl salicylate in a gas state.

The whole or part of the example embodiments disclosed above may be described as, but not limited to, the following supplementary notes.

Supplementary Note 1

A method for sensing methyl salicylate, comprising detecting a reaction product of a terbium-sulfoxide complex represented by the following formula (1) and methyl salicylate;

(1)

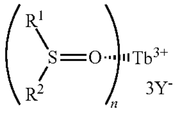

wherein $R^1$ and $R^2$ each independently represent an aliphatic hydrocarbon group having 1 to 8 carbons, or a substituted or unsubstituted aryl group. $R^1$ and $R^2$ may be bonded together to form a ring. $Y^-$ represents a carboxylate ion having 1 to 8 carbons, chloride ion, or nitrate ion. n represents an integer of 1 to 6.

Supplementary Note 2

The method for sensing methyl salicylate according to Supplementary note 1, utilizing a fluorescence emission phenomenon of a complex formed by a reaction of methyl salicylate and the terbium-sulfoxide complex.

Supplementary Note 3

The method for sensing methyl salicylate according to Supplementary note 1 or 2, wherein $Y^-$ in the formula (1) represents acetate ion, propionate ion, butyrate ion, pivalate ion, valerate ion, chloride ion, or nitrate ion.

Supplementary Note 4

A methyl salicylate sensor for detecting methyl salicylate, comprising:

i) a receptor section for methyl salicylate that comprises a terbium-sulfoxide complex represented by the following formula (1); and
ii) a detection section that detects a reaction product of the terbium-sulfoxide complex and methyl salicylate;

(1)

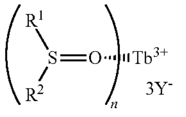

wherein $R^1$ and $R^2$ each independently represent an aliphatic hydrocarbon group having 1 to 8 carbons, or a substituted or unsubstituted aryl group. $R^1$ and $R^2$ may be bonded together to form a ring. $Y^-$ represents a carboxylate ion having 1 to 8 carbons, chloride ion, or nitrate ion. n represents an integer of 1 to 6.

Supplementary Note 5

The methyl salicylate sensor according to Supplementary note 4, wherein the receptor section comprises a paper, a glass, or a resin comprising the terbium-sulfoxide complex represented by formula (1).

Supplementary Note 6

The methyl salicylate sensor according to Supplementary note 4 or 5, wherein $Y^-$ in formula (1) represents acetate ion, propionate ion, butyrate ion, pivalate ion, valerate ion, chloride ion, or nitrate ion.

Supplementary Note 7

The methyl salicylate sensor according to any one of Supplementary notes 4 to 6, the detection section comprising an optical detection element and a computer, wherein the methyl salicylate sensor has a program that causes the computer to execute:

i) receiving a signal from the optical detection element;
ii) analyzing the received signal to determine presence or absence of methyl salicylate and/or a concentration thereof; and
iii) outputting an analysis result.

Supplementary Note 8

A method for detecting pathogen infection in a crop, comprising installing the methyl salicylate sensor according to any one of Supplementary notes 4 to 7 in a vicinity of the crop, and detecting methyl salicylate by the methyl salicylate sensor.

Supplementary Note 9

A program controlling a methyl salicylate sensor, the methyl salicylate sensor at least comprising: a receptor section for methyl salicylate that comprises a terbium-sulfoxide complex represented by the formula (1); and a detection section that detects a reaction product of the terbium-sulfoxide complex and methyl salicylate, the detection section comprising an optical detection element and a computer, wherein the program causes the computer to execute:

i) a step of receiving a signal from the optical detection element;
ii) a step of analyzing the received signal to determine presence or absence of methyl salicylate and/or a concentration thereof; and
iii) a step of outputting an analysis result.

Supplementary Note 10

A detection method for detecting methyl salicylate, comprising:

(i) allowing the terbium-sulfoxide complex represented by formula (1) to react with methyl salicylate to form a methyl salicylate complex;
(ii) exposing the methyl salicylate complex to excitation light; and (iii) detecting fluorescence emitted by the methyl salicylate complex.

Supplementary Note 11

The detection method according to Supplementary note 10, wherein a wavelength in a range of 300 to 400 nm is used as an excitation wavelength of the excitation light.

Supplementary Note 12

The detection method according to Supplementary note 10 or 11, further comprising a step of comparing an intensity of the detected fluorescence with a predetermined reference value to determine a concentration of methyl salicylate.

While the invention has been described with reference to example embodiments and examples thereof, the invention is not limited to these embodiments and examples. Various changes that can be understood by those of ordinary skill in the art may be made to forms and details of the present invention without departing from the spirit and scope of the present invention.

INDUSTRIAL APPLICABILITY

The method for sensing methyl salicylate according to one aspect of the present embodiment uses a predetermined terbium-sulfoxide complex to selectively detect methyl salicylate, which is a plant hormone released by a plant when a plant is infected by a pathogen. The terbium-sulfoxide complex reacts with methyl salicylate to form a methyl salicylate complex and exhibit fluorescence emission, and thus enables selective detection of methyl salicylate.

One aspect of the present embodiment uses a sensor comprising the terbium-sulfoxide complex in a receptor section, thereby enabling early detection of plant disease infection. Specifically, as a sensor that can detect disease infection of a crop at an early stage, it can be used as a novel sensor for agricultural ICT in greenhouses and other horticultural facilities.

The invention claimed is:

1. A method for sensing methyl salicylate, comprising detecting a reaction product of a terbium-sulfoxide complex represented by the following formula (1) and methyl salicylate:

(1)

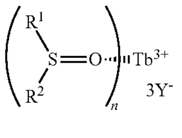

wherein: $R^1$ and $R^2$ each independently represent an aliphatic hydrocarbon group having 1 to 8 carbons, or a substituted or unsubstituted aryl group; $R^1$ and $R^2$ may be bonded together to form a ring; $Y^-$ represents a carboxylate ion having 1 to 8 carbons, chloride ion, or nitrate ion and; n represents an integer of 1 to 6.

2. The method for sensing methyl salicylate according to claim 1, utilizing a fluorescence emission phenomenon of a complex formed by a reaction of methyl salicylate and the terbium-sulfoxide complex.

3. The method for sensing methyl salicylate according to claim 1, wherein Y in the formula (1) represents acetate ion, propionate ion, butyrate ion, pivalate ion, valerate ion, chloride ion, or nitrate ion.

4. A methyl salicylate sensor for detecting methyl salicylate, comprising:

i) a receptor section for methyl salicylate that comprises a terbium-sulfoxide complex represented by the following formula (1); and ii) a detection section that detects a reaction product of the terbium-sulfoxide complex and methyl salicylate;

(1)

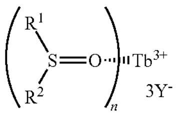

wherein; $R^1$ and $R^2$ each independently represent an aliphatic hydrocarbon group having 1 to 8 carbons, or a substituted or unsubstituted aryl group; $R^1$ and $R^2$ may be bonded together to form a ring; Y represents a carboxylate ion having 1 to 8 carbons, chloride ion, or nitrate ion and; n represents an integer of 1 to 6.

5. The methyl salicylate sensor according to claim 4, wherein the receptor section comprises a paper, a glass, or a resin comprising the terbium-sulfoxide complex represented by formula (1).

6. The methyl salicylate sensor according to claim 4, wherein $Y^-$ in formula (1) represents acetate ion, propionate ion, butyrate ion, pivalate ion, valerate ion, chloride ion, or nitrate ion.

7. The methyl salicylate sensor according to claim 4, the detection section comprising an optical detection element and a computer, wherein the methyl salicylate sensor has a program that causes the computer to execute:

i) receiving a signal from the optical detection element;

ii) analyzing the received signal to determine presence or absence of methyl salicylate and/or a concentration thereof; and iii) outputting an analysis result.

8. A method for detecting pathogen infection in a crop, comprising installing the methyl salicylate sensor according to claim 4 in a vicinity of the crop, and detecting methyl salicylate by the methyl salicylate sensor.

9. The methyl salicylate sensor according to claim 4, wherein the detection section optically detects a fluorescence emission of the reaction product of the terbium-sulfoxide complex and methyl salicylate.

* * * * *